(12) United States Patent
Petrigni et al.

(10) Patent No.: US 7,132,412 B2
(45) Date of Patent: Nov. 7, 2006

(54) TREATMENT OF SKIN DISEASES USING A PHARMACEUTICAL PREPARATION IN COLLOIDAL FORM

(76) Inventors: Giuseppe Petrigni, 20123 Milano Via Fontana, 1 Italia, Milan (IT); Luigi Allegra, 20123 Milano Via DeAmicis 12 Italia, Milan (IT)

( * ) Notice: Subject to any disclaimer, the term of this patent is extended or adjusted under 35 U.S.C. 154(b) by 107 days.

(21) Appl. No.: 10/650,812

(22) Filed: Aug. 29, 2003

(65) Prior Publication Data

US 2004/0136925 A1    Jul. 15, 2004

(30) Foreign Application Priority Data

Aug. 30, 2002   (IT)   .................... MI2002A1866

(51) Int. Cl.
*A61K 31/715*    (2006.01)
*A61K 31/728*    (2006.01)

(52) U.S. Cl. .................. 514/54; 514/861; 514/863; 536/53; 536/55.1; 536/55.2

(58) Field of Classification Search .............. 514/54, 514/861, 863; 536/53, 55.1, 55.2
See application file for complete search history.

(56) References Cited

U.S. PATENT DOCUMENTS 4,141,973 A  *  2/1979  Balazs ..................... 514/54
5,728,391 A  *  3/1998  Ikeya et al. .............. 424/401

* cited by examiner

*Primary Examiner*—Shaojia Anna Jiang
*Assistant Examiner*—Michael C. Henry
(74) *Attorney, Agent, or Firm*—Michael G. Gilman

(57) ABSTRACT

A new use of a suitable colloidal mixture of hyaluronic acids, of different molecular weights mixed together in a proper ratio in the treatment of the cutaneous diseases is described.

12 Claims, No Drawings

TREATMENT OF SKIN DISEASES USING A PHARMACEUTICAL PREPARATION IN COLLOIDAL FORM

The present invention relates to a pharmaceutical preparation in colloidal form, useful in the treatment of skin pathological, diseases. The pharmaceutical preparation object of the present invention contains, as active ingredient, a suitable mixture of hyaluronic acids of various molecular weight, properly added with suitable diluents, which demonstrated to possess an interesting antiflogistic, antioxidant and tissue repair activity.

A further object of the present invention is the use, in the treatment of pathological skin disease, of the pharmaceutical preparation of the present invention, by topic and/or general administration.

Hyaluronic acid is a natural biopolymer having a number of biological functions in bacteria and in superior animals, including man; it can be found in tissues of superior animals, where it feels, in particular, the intercellular spaces. Hyaluronic acid is practically present in any part of the living organism, where its distribution is practically ubiquitous in tissues and in parenchymal organs with a higher concentration in lax connective tissue and in particular in the vitreous humour and in joint sinovial fluid. Hyaluronic acid levels ill serum are normally 10–100 mcg/liter.

The adult human organism skin, where about 25 mg hyaluronic acid per epidermis gram of weight and 118 mg hyaluronic acid per derma gram of weight are found, represents the highest accumulation site. Hyaluronic acid can be extracted, as it has been traditionally made until a few years ago, from a natural source, such as rooster crests or bovine connective tissues, by using isolation methods, that include an enzymatic digestion, a specific separation to remove proteins and a purification to obtain the crude extract: these steps present a lot of disadvantages, connected to the cost, to the bad control of the molecular weight and to the risk of viral infections. Hyaluronic acid can also the produced through a biotechnological process, such as biofermentation, that is the fermentation of Gram+bacteria, as Streptococcus, by which hyaluronic acid biopolymers are obtained in a theoretically unlimited amount, with a molecular weight from 1 to 4 MDa, without the above limiting factors.

Hyaluronic acid is a member of the glucosaminoglyeans family, formed by polyanionic, linear, not branched, disaccharide chains, with a molecular weight from hundreds to thousands of millions dalton, in which disaccharidic units are repeated, formed by N-acetylglucosamine and glucuronic acid connected by glycosidic bonds. Unlike other glucosaminoglycans, hyaluronic acid contains no sulphate groups, is free from covalent bonds with proteins and is considered to have, among the mucopolysaccbaridic compounds, the simplest chemical structure.

In body tissues, hyaluronic acid is found bound to cell membranes, joined to other macromolecules, or as free polysaccharide. It is unique in its ability to bond and retain large amount of water in the interfibrillar spaces, up to 6 liters per gram of hyaluronic acid, thus forming, the backbone of the amorphous colloidal matrix acting as cement between cells and connective fibres with relevant effects on microcirculatory exchanges, thanks to its influence on the interstitial volume, water conductivity and macromolecule diffusion. Within the skin, aqueous solutions of hyaluronic acid give rise to gels that act as dampers.

Hyaluronic acid plays an important role in the body, both for its mechanical and transport properties. It has shown to be important in a number of tissue functions, such as hydration, lubrication, solute transport, cell migration and detachment; it also plays a central role in controlling cell growth and differentiation, in tissue morphogenesis Hyaluronic acid solutions are typically viscoelastic and pseudoplastic. The viscoclastic property of hyaluronic acid solutions, important in its use as biomaterial, is determined by the concentration and the molecular weight of its chains. The molecular weight of hyaluronic acid of different origin is widely spread and highly variable, ranging from 10,000 to 10,000,000 Da.

It is known the use of hyaluronic acid in orthopedy for osteoarthrytis therapy (intraarticular injections), ophthalmology (intraocular injections) and in the prevention of post-surgical abdominal adherences.

It has now been found, and this is the object of the invention, that pharmaceutical preparations containing a suitable mixture, in colloidal form, of biopolymerized hyaluronic acids, having defined and different molecular weights and being dispersed in suitable diluents, have an interesting antiflogistic, antioxidant and of tissue repair activities, that make them particularly effective in the treatment of pathological cutaneous diseases, such as erythematous and erythema-squamous eruptions, vasicular eruptions, papular eruptions, pustular eruptions, blistered eruptions, ulcerous eruptions, in metabolic diseases, nodular eruptions, skin mycotic diseases, tumoral eruptions, hair and scalp diseases, cutaneous rashes related to systemic diseases (collagenopathies), pediatric dermatosis, geriatric dermatosis, dermatological emergencies. Specific examples of the above mentioned pathologies are nettle-rash, atopic eczema, contact dermatitis, dyshidrosis, Herpes simplex, lichen, itch, acne vulgaris, pemphigus, ulcerous eruptions from arteriosclerosis and bedsores, actinomycosis, furuncles, suppurative hydroadenitis, Candidiasis, keloids, fungous mycosis, scleroderma, ichthyosis, xerotye dermatitis, wounds, grazes, bums and dermatitis due to insect bites and medusa contact, cicatrices, etc.

Examples of suitable diluents of the hyaluronic acid mixture are distilled water, saline solution, dimethylsulphoxide or alcoholic solutions.

The pharmaceutical preparation in colloidal liquid form object of the invention, is preferably administered by topical route; however, optionally added with suitable pharmaceutically acceptable known diluents, it may be conveniently administered through a general route, such as subcutaneous intramuscular intradermal infection, or in a solid form by oral route or as a transdermal plaster by transcutaneous route.

In fact, for some therapeutic indications, an administration by a general route, associated with a topical administration, is required. More specifically, the hyaluronic acids of the mixture have molecular weight ranging from 200 kDa to 4,000 kDa; such hyaluronic fractions are mixed together in defined ratios depending on their molecular weight. Among the preferred pharmaceutical preparations of the present invention, preparations are included, which contain mixtures of hyaluronic fractions having molecular weight multiple in respect to the molecular weight of the hyaluronic fraction having the lowest molecular weight. Among these fractions the more preferred ones are those which are each other in ratio 1:1 and have a molecular weight of 400 kDa and its multiples. In general, the number of hyaluronic fractions of different molecular weight which forms the mixture can widely vary, as well as it varies the ratio according to which they are mixed. The number of hyaluronic fractions of different molecular weight present into the mixture varies preferably from 2 to 9, and more preferably from 5 to 7.

The following Example is aimed to describe in more details the invention, without limiting it.

EXAMPLE 1

Preparation of 10 % Colloidal Hyaluronic Acid

Different solution- of hyaluronic acid of molecular weight ranging between 400 and 4,000 kDa were previously prepared.

The procedure is essentially based on a condensation reaction between glucuronic acid of vegetal origin and a solution of hydrolized chitin (85–90 %, acetylglucsamine on the dry), with a biological catalyst, at a temperature between 18 and 20° C.

The mixture obtained is substantially formed by about 90% of a disaccharide having a structure identical to that of the base monomer of the hyaluronic acid and the remaining 10% on the dry of polymers of the same monomer up to 4,000 kDa. This mixture, at 10% in aqueous solution, is a colloidal and transparent fluid. The above proportions between monomer and polymers were kept and chosen to optimize the viscosity of the preparation, without affect the required performance.

Grams 890 demineralized water are, plaged in a stainless-steel turboemulsifier, the melter temperature is brought to 18–20° C. and made under vacuum. The mixer is switched on at low speed and, after checking the temperature (18–20° C.) 100 g of the mixture of hyaluronic acids and 10 g methyl parabenzoate are slowly added thereto. The obtained mass is homogenized at low speed for about 5 minutes and, when homogenization is completed, the mixer is kept on for another 30 minutes at low speed The obtained product is kept under vacuum for 60 minutes and then it is discharged from the equipment Viscosity ($\eta$) and elasticity (G) if the preparation, at various temperatures were evaluated. No correlation between temperature and elasticity was evidenced, while an inverse correlation between viscosity and temperature appeared, taking into account that the preparation is obtained at 18–20° C. Spinnability of said colloidal composition was also determined.

| | Viscosity ($\eta$): | | |
|---|---|---|---|
| at 5° C. | $\eta$ (mPas) | 7200.20 | (immediate) |
| | $\eta$ (mPas) | 6446.77 | (after 5 min) |
| at 21° C. | $\eta$ (mPas) | 6001.79 | (immediate) |
| | $\eta$ (mPas) | 5931.37 | (after 5 min) |
| at 37° C. | $\eta$ (mPas) | 5676.34 | (immediate) |
| | $\eta$ (mPas) | 5642.63 | (after 5 min) |

Spinnability at room temperature: 18 mm.

Here below the result are reported relevant to treatments performed administering the preparation of the invention on patients affected by specific pathologies.

Acne vulgaris: Seven patients, five adolescents (three females, aged 14, 16 and 17, two males, aged 16 and 19, respectively) and two adult males, aged 26 and 30, were investigated. All patients were suffering acne on the face, in a new acute phase. The two adults had also acne lesions on the upper chest.

The five adolescents were affected by mild severe acne on the face, with partially erythematous, seborroic, greasy, shiny skin with comedos (white and black spots) with papular-pustular lesions; some papules were intense red, others purple red that evidenced the resolution stage of previous lesions.

The two adults, with acetic lesions, both on the face and on the upper part of the chest, were affected by a severe acne and their skin was shiny, greasy, erythematous and seborroic with polymorphic eruption of comedos (white and black spots) and with several superficial as well as deep papules in phlogosis condition, pustular elements and two small cysts with atrophic cicatricial lesions in one of the two patients. Such symptoms became more severe and prolonged in the time because the patients, due to the anxiety for the presence of antiaesthetic lesions, were inclined to crush the pustules, trying free them from the pus.

All patients were submitted to a proper and balanced diet, with the elimination of food that could cause the acne worsening, and treated for 10 days with two topical-l applications (face and chest) per day of the colloidal preparation of hyaluronic acid of the invention, after washing the anatomic lesions with warm water and soap. An adult was previously plucked on the chest before treatment.

All patients were daily controlled, and so it was possible to daily evaluate the improvements of the skin, consisting in a progressive, gradual reduction of the phlogistic lesions, both in toto and on the single elements of the lesions, in particular, oil the papular-pustular ones.

Contact eczema: Three patients, a man and two women, aged 30, 37 and 45 respectively, were treated. The man had for about 20 days an exudative erythema-vescicular eruption on the armpits; the patch test was positive to a deodorant. The woman aged 37 had for one month erythema-vescicular spots localized on the superior and inferior eyelid regions, trending to spread down the face; the patch test resulted to be positive to cosmetics. The 45 aged woman presented for some months a significant erythema-vescicular eruption on the lobes of the ears and in part in the bordering areas of the neck; the patch test was positive to nickel.

All patients, even though after diagnosis all contacts with allergicing agent were, if possible, avoided, were treated for 10 days, in the acute phase of the eczematous dermatitis with two topical treatments per day of the colloidal solution of hyaluronic acid according to the invention, being the man previously submitted to armpit depilation All patients showed a significant regression of the erythema-vescicular lesions; the clinical improvement being very evident, day by day, during the treatment.

Psoriasis: Two male patients, aged 40 and 52 respectively, were examined. Both were affected by psoriasis since adolescence and both were medium-high level professionals and submitted for several years to significant emotional stresses. They were neither drinkers nor smokers. The lesions were spread nearly on all the body, from elbows to knees, on the scalp, buttocks, umbelicus, trunk and upper and lower limbs and were characterized by areas with red spots and papules covered by small, dry and white squamas, areas with wider lesions, merging together to give spots having polyceltric (geographical) edges with increased desquamation and areas, such as elbows, that showed typical psoriasis plaques, having whitish-silver squamas with well defined geographical edges. Both patients complained of itches of variable intensity and both were treated for 10 days on the elbows and on the extensor areas of the forearms with the colloidal preparation of hyaluronic acid, according to the invention, topically administered twice a day.

The elbows with psoriasis plaques were pretreated, 10 minutes before the application with the colloidal preparation containing hyaluronic acid, according to the invention, only in the morning and only for the first three days, with a 30% glycolic acid solution, spread with a small brush, in order to help reductio-elimination of the psoriasis plaques and the penetration of the hyaluronic acid. The treatments resulted to be effective on both patients, showing a good anti-inflammatory activity as well as a good cutaneous rehydratation of the treated areas with a significant reduction of the erythema-papular and of the squamous symptoms.

Atopical eczema

Infancy eczema: Three patients, two males and one female, aged between 7 months and 2 years, were treated. All patients showed a familiar allergic anamnesis, which involved both parents. All of them showed cutaneous eruptions on the face a well as on the neck and trunk, in form of crythematous spots, isolated and partially merging together, exuding and/or crusty, strongly itching. One male had also asthmatic symptoms, for which he was treated by aerosol treatment with 2β-stimulants and steroids with topical activity.

All patients had been previously topically treated with steroids (which treatment was discontinued at least three weeks before) and hydrating creams; all patients were allergic to cow milk and were fed with soy milk.

Among the lesions, only those on the face and neck were treated with two topical applications per tiny of a colloidal solution of hyaluronic acid according to the invention, after washing the face and neck with lukewarm water containing starch.

All patients were daily examined and this allowed to evaluate the daily improvements of the eczemalous lesions obtained by the treatment and characterized by a significant and progressive reduction of the erythematous, crusty and exudative lesions in respect to the eczematous lesions present in the areas not submitted to the treatment.

Early childhood eczema: Three patients, one male and two females, aged between 7 and 9 years were treated. All patients showed a familiar allergic anamnesis, which involved both parents.

All patients showed erythema-papular lesions, partially lichenificated, with hyperpigmented spots, dry skin, strongly itching with scratching grazes on the face, neck, popliteal cavity, elbow folds, hands and trunk.

All patients had also respiratory allergic seasonal pathologics in spring (pollinosis) and resulted to be positive to the allergy tests and to the Graminae pollen. No patient was under a specific immunotherapy treatment. All patients did not use any drug for at least 10 days. Only the lesions on the hands and on elbow folds, were treated, after washing with lukewarm water containing starch, with two topical applications per day of a colloidal solution of hyaluronic acid according to the invention.

All patients were daily examined to evaluate the progressive improvements of the erythema-papular lesions and of the lesions due to the skin scratching and the disappearance of the itch in the treated areas.

From the above it is proved that the colloidal solutions containing hyaluronic acid mixtures of different molecular weights, object of the present invention, when topically administered to patients suffering from cutaneous diseases of various kind, resulted therapeutically effective, determining significant improvements, up to the complete healing of the sames

The invention claimed is:

1. A method of treating a cutaneous disease comprising administering by topical, general, oral or transdermal means to an animal in need thereof an effective amount of a colloidal therapeutic composition comprising a mixture comprising:
   a mixture of plural aliquots of different molecular weight biopolymerized hyaluronic acids in colloidal form; and
   a dispersing amount of at least one diluent selected from the group consisting of distilled water, saline solution, dimethylsulphoxide and alcoholic solutions;
   wherein said biopolymerized hyaluronic acid aliquots have different molecular weights in the range of about 200 kDa to 4,000 kDa and at least some of said biopolymers in different aliquots have molecular weights that are multiples of the molecular weight of the aliquot of hyaluronic acid having the lowest molecular weight present in said mixture.

2. The method as claimed in claim 1 comprising about 2 to 9 aliquots of said colloidal, biopolymerized hyaluronic acids having multiple molecular weights, based on the molecular weight of the aliquot with the lowest molecular weight.

3. The method as claimed in claim 1 comprising about 5 to 7 aliquots of said colloidal, biopolymerized hyaluronic acids having multiple molecular weights, respectively, based on the molecular weight of the aliquot with the lowest molecular weight.

4. The method as claimed in claim 1 wherein the colloidal, biopolymerized hyaluronic acid aliquots have molecular weights that are related to each other in a unitary ratio.

5. The method as claimed in claim 1 wherein the colloidal biopolymerized hyaluronic acids have molecular weights of 400 kDa, 800 kDa, 1200 kDa, 1600 kDa, and 2000 kDa respectively and are present in said mixture in ratios of 1:1:1:1:1.

6. The method as claimed in claim 1 wherein said animal is a mammal.

7. The method as claimed in claim 1 wherein said animal is human.

8. The method as claimed in claim 1 wherein said composition is administered topically.

9. The method as claimed in claim 1 wherein said composition is administered orally.

10. The method of claim 1 wherein said composition is administered transdermally.

11. The method as claimed in claim 1 wherein said composition is administered by a general route.

12. The method as claimed in claim 1 wherein said composition further comprises an additional diluent.

* * * * *

UNITED STATES PATENT AND TRADEMARK OFFICE
CERTIFICATE OF CORRECTION

PATENT NO. : 7,132,412 B2
APPLICATION NO. : 10/650812
DATED : November 7, 2006
INVENTOR(S) : Giuseppi Petrigni et al.

It is certified that error appears in the above-identified patent and that said Letters Patent is hereby corrected as shown below:

• column 1, line 42: add a comma after "obtained";

• column 1, line 45: change "glucosaminoglyeans" to --glucosaminoglycans--

• column 1, line 61: add a comma after "fibres";

• column 2, line 4: after "morphogenesis" add --and in healing processes.--;

• column 2, line 13: after "injections)," add --in--;

• column 2, line 24: change "vasicular" to --vesicular--;

• column 2, line 36: change "xerotye" to --xerotyc--;

• column 2, line 37: change "bums" to --burns--;

• column 2, line 47: after "subcutaneous" add a comma (--,--) ;

• column 2, line 48: after "intramuscular" add a comma (--,--);

• column 2, line 48: change "infection" to --injection--;

• column 3, line 10: change "solutions" to --solution--;

• column 3, line 27: after "are" delete the comma (",");

• column 3, line 27: change "plaged" to --placed--;

• column 3, lines 29, 31, 49, 51 and 53: change "C." to --C--;

• column 3, line 37: change "equipment" to --equipment.--;

• column 3, line 38: change "if" to --of--;

• column 3, line 57: change "result" to --results--;

• column 4, line 5: change "acetic" to --acneic--;

• column 4, line 18: change "topical-I" to --topical--

• column 4, line 27: change "oil" to --on--;

UNITED STATES PATENT AND TRADEMARK OFFICE
CERTIFICATE OF CORRECTION

PATENT NO. : 7,132,412 B2
APPLICATION NO. : 10/650812
DATED : November 7, 2006
INVENTOR(S) : Giuseppi Petrigni et al.

It is certified that error appears in the above-identified patent and that said Letters Patent is hereby corrected as shown below:

• column 4, lines 30, 32, 36, and 46: change "vescicular" to --vesicular--;

• column 4, line 57: change "polyceltric" to --polycentric--;

• column 5, line 7: change "rehydratation" to --rehydration--;

• column 5, line 15: change "a" to --as--;

• column 5, line 16: change "crythematous" to --erythematous--;

• column 5, line 26: change "tiny" to --day--;

• column 5, line 31: change "eczemalous" to --eczeratous--;

• column 5, line 45: change "pathologics" to --pathologies--;

• column 6, line 13: delete "in colloidal form";

• column 6, line 16: change "solutions" to --solution--;

• column 6, lines 25, 30, 35 and 37: delete "colloidal"; • column 6, line 39: change "weights" to --weight--.

Signed and Sealed this

Twenty-fourth Day of July, 2007

JON W. DUDAS
*Director of the United States Patent and Trademark Office*

UNITED STATES PATENT AND TRADEMARK OFFICE
CERTIFICATE OF CORRECTION

PATENT NO.       : 7,132,412 B2
APPLICATION NO. : 10/650812
DATED            : November 7, 2006
INVENTOR(S)      : Giuseppi Petrigni et al.

It is certified that error appears in the above-identified patent and that said Letters Patent is hereby corrected as shown below:

Column 1, line 42: add a comma after "obtained";

Column 1, line 45: change "glucosaminoglyeans" in --glucosaminoglycans--

Column 1, line 61: add a comma after "fibres";

Column 2, line 4: after "morphogenesis" add --and in healing processes.--;

Column 2, line 13: after "injections)," add --in--;

Column 2, line 24: change "vasicular" to --vesicular--;

Column 2, line 36: change "xerotye" to --xerotyc--;

Column 2, line 37: change "bums" to --burns--;

Column 2, line 47: after "subcutaneous" add a comma ",";

Column 2, line 48: after "intramuscular" add a comma ",";

Column 2, line 48: change "infection" to --injection--;

Column 3, line 10: change "solution" to --solutions--;

Column 3, line 27: after "are" delete the comma ",";

Column 3, line 27: change "plaged" to --placed--;

Column 3, lines 29, 31, 49, 51 and 53: change "C." to --C--;

Column 3, line 37: change "equipment" to --equipment.--;

Column 3, line 38: change "if" to --of--;

Column 3, line 57: change "result" to --results--;

Column 4, lines 30, 32, 36, and 46: change "vescicular" to --vesicular--;

Column 4, line 57: change "polyceltric" to --polycentric--;

UNITED STATES PATENT AND TRADEMARK OFFICE
CERTIFICATE OF CORRECTION

PATENT NO. : 7,132,412 B2
APPLICATION NO. : 10/650812
DATED : November 7, 2006
INVENTOR(S) : Giuseppi Petrigni et al.

It is certified that error appears in the above-identified patent and that said Letters Patent is hereby corrected as shown below:

Column 5, line 7: change "rehydratation" to --rehydration--;

Column 5, line 15: change "a" to --as--;

Column 5, line 16; change "crythematous" to --erythematous--;

Column 5, line 28: change "tiny" to --day--;

Column 5 line 31: change "eczemalous" to --eczeratous--;

Column 5 line 45: change "pathologics" to --pathologies--;

Column 6, line 13: delete "in colloidal form";

Column 6, line 16: change "solutions" to --solution--;

Column 6, lines 25, 30, 35, and 37: delete "colloidal"; and

Column 6, line 39: change "weights" to --weight--.

Signed and Sealed this

Fourth Day of December, 2007

JON W. DUDAS
*Director of the United States Patent and Trademark Office*